United States Patent
Wada et al.

(10) Patent No.: US 6,432,076 B1
(45) Date of Patent: Aug. 13, 2002

(54) APPLICATOR FOR TAMPONS

(75) Inventors: Mitsuhiro Wada; Ayami Suga, both of Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 0 days.

(21) Appl. No.: 09/710,576

(22) Filed: Nov. 9, 2000

(30) Foreign Application Priority Data

Nov. 19, 1999 (JP) .......................................... 11-329275

(51) Int. Cl.[7] ................................................. A61F 13/20
(52) U.S. Cl. ........................................................ 604/15
(58) Field of Search ............................ 604/11–18, 904, 604/57–60, 285–288, 311

(56) References Cited

U.S. PATENT DOCUMENTS

| 3,628,533 A | * | 12/1971 | Ioyer .......................... 604/15 |
| 4,921,474 A | * | 5/1990 | Suzuki et al. ................. 604/15 |
| 5,267,953 A |   | 12/1993 | Paul et al. .................... 604/15 |
| 5,437,628 A | * | 8/1995 | Fox et al. ..................... 604/14 |

FOREIGN PATENT DOCUMENTS

| GB | 549053 | 11/1942 |
| GB | 1016867 | 1/1966 |

* cited by examiner

*Primary Examiner*—Dennis Ruhl
(74) *Attorney, Agent, or Firm*—Darby & Darby

(57) ABSTRACT

Provided is an applicator for a tampon including an outer cylinder having a protruding mouth at a leading end thereof, through which a tampon is pushed out and an opening at a root end thereof; and an inner cylinder for pushing out the tampon which has a front end located in the outer cylinder and a rear end protruding rearwardly from the outer cylinder through the opening. The inner cylinder is formed of an extruded material which is extrusion-molded of a thermoplastic resin into a cylindrical shape, and is provided at the front end thereof with a push portion which is deformed to have a larger diameter from the extruded material.

9 Claims, 4 Drawing Sheets

APPLICATOR FOR TAMPONS

BACKGROUND OF THE INVENTION

1. Field of the Invention

The present invention relates to a tampon applicator to be employed when a sanitary tampon is to be inserted into a human body.

2. Description of the Related Art

The applicator for the sanitary tampon is constructed to include an outer cylinder for fitting the tampon therein, and an inner cylinder inserted into the outer cylinder and protruding rearwardly from the root end of the outer cylinder. A take-out cord, as extended from the tampon, is led out of the outer cylinder through the inner cylinder and protruded rearwardly from a rear end of the inner cylinder.

When the tampon is to be employed, the outer cylinder is inserted into a vaginal cavity, and the inner cylinder is pushed to push the tampon out of the outer cylinder. Then, the tampon is inserted into the vaginal cavity while expanding a number of deformable valves at the leading end of the outer cylinder.

Some of the existing applicators are formed to have an outer cylinder and an inner cylinder which are made of paper. In recent years, however, an outer cylinder injection-molded of a synthetic resin has been employed so that it may have a smooth surface and may be smoothly inserted into the vaginal cavity. In this case, the inner cylinder is also generally formed by the injection-molding method.

However, the inner cylinder of the applicator takes a high molding cost if it is injection-molded of a synthetic resin, because the mold to be employed for the injection molding is expensive. When the diameter of the inner cylinder or the diameter of the push portion at the leading portion of the inner cylinder has to be changed for changing the shape of the product, on the other hand, the mold has to be remade to increase the cost for this design change.

On the other hand, since the tampon applicator is dumped after use, it is preferable for the environment to minimize the amount of resin to be employed. Accordingly, by making at least the inner cylinder thin and diametrically small, it is possible to reduce the amount of resin to be employed. However, the injection-molding method cannot realize the thin, diametrically small inner cylinder, because of the following reasons:

(1) Upon forming the inner cylinder by the injection-molding method, a plurality of the inner cylinders are simultaneously injection-molded at one shot of a molten resin. Accordingly, in order to stabilize the quality of the molded inner cylinders while keeping the satisfactory fluidity of the resin in the mold, the thickness of the inner cylinders have to be enlarged to a considerable extent, so that it is essentially impossible to injection-mold the inner cylinders having a thickness of 0.6 mm or less. On the other hand, if the external diameter of the inner cylinder is reduced, the passage for the cooling water cannot be formed in the cored mold (or insert die) which is located on the inner side of the inner cylinder upon injection-molding. As a result, it takes a long time to cool the mold, so that the cycle time for the injection-molding is expanded to degrade the molding efficiency.

(2) On the other hand, in case of the injection-molding, it is difficult to orient the resin in the axial direction of the inner cylinder, so that the molded inner cylinder cannot be strengthened in the axial direction thereof. Accordingly, if the inner cylinder is made thin and diametrically small, the inner cylinder is easily buckled and deformed in the axial direction when it is put out of the mold after injection-molding. On the other hand, if the inner cylinder has a low axial strength, there is a possibility of being buckled and folded when the inner cylinder pushes out the tampon to be employed.

SUMMARY OF THE INVENTION

The invention has an object to provide a tampon applicator which can manufacture the inner cylinder at low cost, can enhance the buckling strength in the axial direction even when the inner cylinder is made thin and diametrically small, and can easily deform the shape of the inner cylinder according to the change in the shape of the outer cylinder.

According to an aspect of the invention, an applicator for a tampon may comprise: an outer cylinder including a protruding mouth at a leading end thereof, through which a tampon is pushed out and an opening at a root end thereof; and an inner cylinder for pushing out the tampon which has a front end located in the outer cylinder and a rear end protruding rearwardly from the outer cylinder through the opening, wherein the inner cylinder is formed of an extruded material which is extrusion-molded of a thermoplastic resin into a cylindrical shape, and is provided at the front end thereof with a push portion which is deformed to have a larger diameter from the extruded material.

For example, the outer cylinder includes a large diameter portion for fitting the tampon therein, and a small diameter portion extending from the large diameter portion toward the root end, and wherein the push portion of the inner cylinder is positioned in the large diameter portion and has a larger external diameter than an internal diameter of the small diameter portion.

According to the invention, the inner cylinder of the applicator is made of the excluded material of the thermoplastic resin so that the cost for manufacturing the inner cylinder can be lowered. On the other hand, the extruded material can freely select the thickness and the external diameter in comparison with the injection-molding, so that the thin, diametrically small inner cylinder can be formed with a smaller amount of employed resin. Furthermore, the inner cylinder made of the extruded material of the thermoplastic resin can be easily formed with the diverging push portion at the front end which is located within the outer cylinder.

On the other hand, it is preferable that the extruded material is extrusion-molded and then axially oriented.

Since the resin is oriented in the axial direction of the inner cylinder, the axial strength of the inner cylinder can be enhanced, and the buckling strength thereof can also be enhanced even if it is made thin and diametrically small. Accordingly, in process of manufacturing or at the time of using the inner cylinder, it can prevent the inner cylinder from being folded due to the buckling.

Moreover, it is preferable that an external diameter of the push portion is gradually diverged toward the front end.

With this shape, the push portion can be simply shaped merely by heating and pushing a press die having a tapered portion, for example, onto the front end of the inner cylinder.

Moreover, the inner cylinder can also be provided at the rear end with a diverging portion which is deformed to have a diameter gradually enlarged toward the rear end.

In this case, it is preferable that the diverging portion formed at the rear end of said inner cylinder have an edge portion which is bent outwardly or inwardly of the diverging portion.

When the applicator is to be used, the user pushes the rear end of the inner cylinder with the finger. If the edge portion of the diverging portion is bent, the edge portion of the inner cylinder will not contact with the finger to reduce the resistance to the finger. Accordingly, the tampon can be easily inserted into the vaginal cavity.

Moreover, it is preferable that the push portion formed at the front end of the inner cylinder have an edge portion which is bent outwardly or inwardly of the push portion.

When the applicator is employed to insert the tampon into the vaginal cavity, the edge portion of the push portion at the front end of the inner cylinder may contact with a portion of the user's body. In this case, the uncomfortable feeling, as might otherwise be caused by the contact with a portion of the body, is eliminated if the edge portion is bent.

In this case, it is preferable that a bent portion which is bent outwardly or inwardly of the push portion has a width size smaller than a thickness of a take-out cord extending from said tampon.

In manufacturing process, the take-out cord of the tampon is inserted from the outer cylinder into the inner cylinder. At this time, the width size of the bent portion at the front end of the inner cylinder is made smaller than the thickness of the cord, so that it prevents the take-out cord from being caught in the clearance between the bent portion and the inner wall of the outer cylinder. As a result, it becomes easy to insert the tampon into the applicator.

DESCRIPTION OF THE PREFERRED EMBODIMENT

Figure 1:
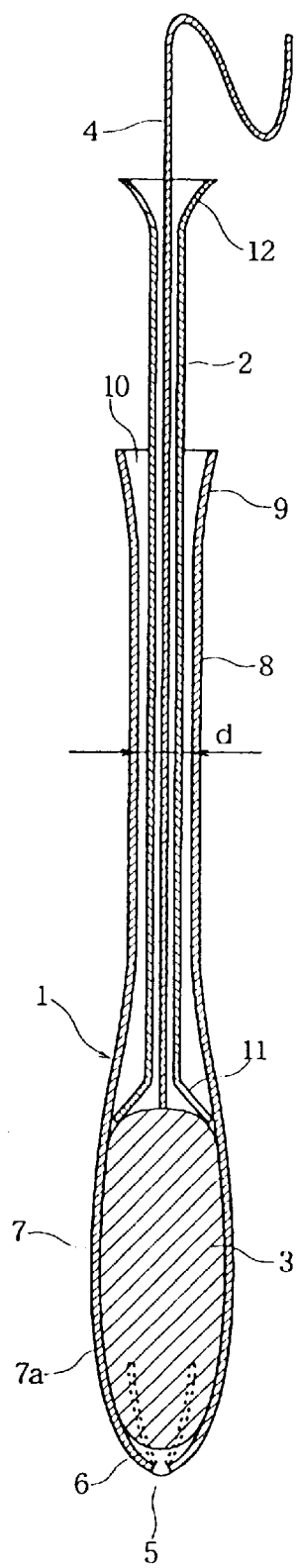
FIG. 1 is a longitudinal section showing the state in which a tampon is fitted in a tampon applicator according to the invention.
Figure 2A:
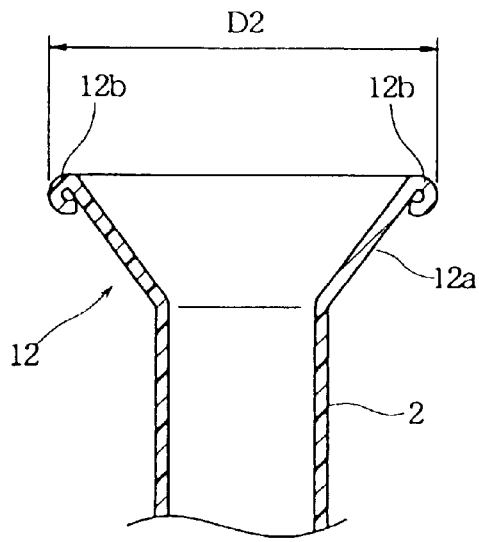
FIG. 2A is an enlarged section showing a diverging portion of the rear end of an inner cylinder.
Figure 2B:
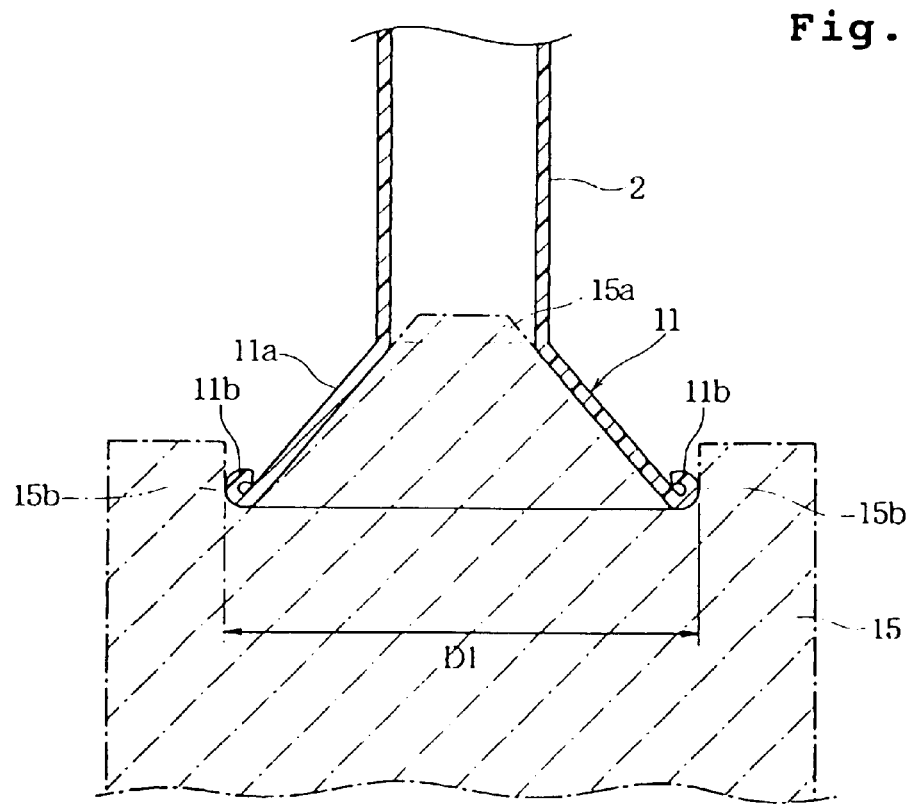
FIG. 2B is an enlarged section showing a push portion of the front end of the inner cylinder.
Figure 3:
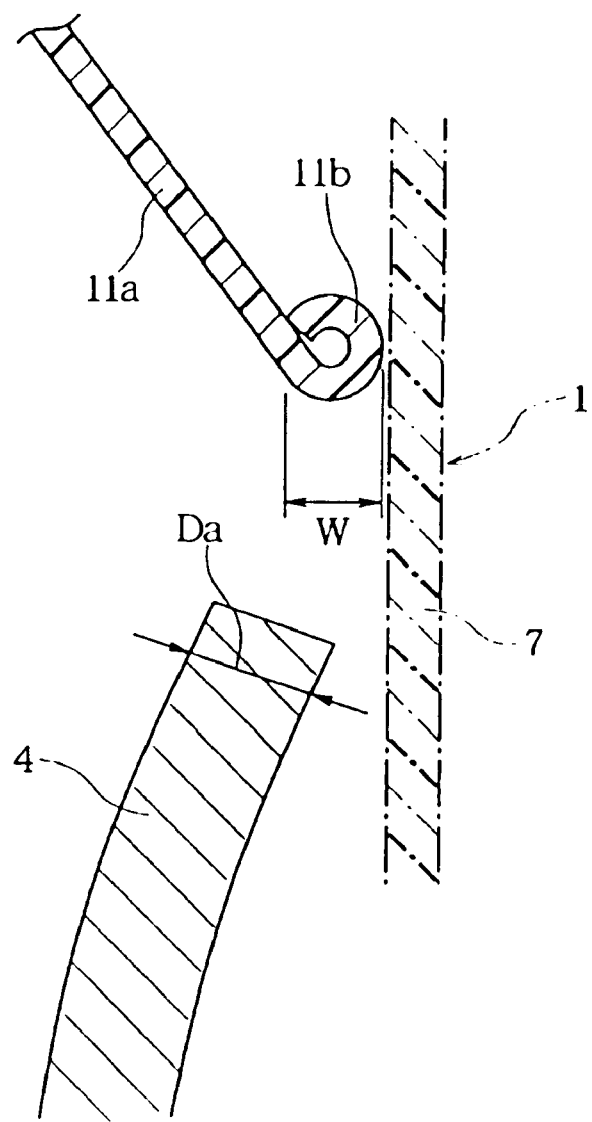
FIG. 3 is an enlarged section showing a slide portion between the push portion at the front end of the inner cylinder and the inner wall of the outer cylinder.

FIG. 1 is a longitudinal section showing the state in which a tampon is fitted in an applicator according to the invention; FIGS. 2A and 2B are enlarged sections showing the rear end and the front end of an inner cylinder of the applicator; FIG. 3 is an enlarged section showing the shape of the edge portion of the push portion at the front end of the inner cylinder; and FIGS. 4A, 4B, 4C and 4D are explanatory diagrams showing one embodiment of a method for manufacturing the applicator.

The tampon applicator, as shown in FIG. 1, is constructed to include an outer cylinder 1 and an inner cylinder 2. In the leading portion of the outer cylinder 1, there is fitted a tampon 3 which is formed by compress-molding absorptive fibers such as cotton. To this tampon 3, there is connected a take-out cord 4 which is extended rearwardly from the inside of the outer cylinder 1 through the inner cylinder 2.

The outer cylinder 1 is injection-molded of a thermoplastic resin such as the PE (polyethylene) or the PP (polypropylene). The outer cylinder 1 thus injection-molded is smooth on its surface but is not sharp at the edge portions of valves 6 around an end protruding mouth 5 provided at the leading portion of the outer cylinder 1, thereby to give little uncomfortable feeling when it comes into contact with the human body. The thermoplastic resin is preferably exemplified by the LDPE (i.e., low density polyethylene) when the outer cylinder 1 is injection-molded, so that the resin may flow without stagnation in the mold thereby to provide a smooth surface and a thickness as small as possible. The thickness of the outer cylinder 1 to be formed by the injection-molding is within a range of 0.6 mm to 1.0 mm.

At the leading portion of the outer cylinder 1, there is formed a large diameter portion 7 for fitting the tampon 3 therein, and this large diameter portion 7 forms a curved face portion 7a at its leading portion. The large diameter portion 7 is provided at its leading end with the protruding mouth 5 through which the tampon 3 is pushed out, and the curved face portion 7a is provided with a plurality of the deformable valves 6 in a petal shape. Immediately after the outer cylinder 1 is injection-molded, as shown in FIG. 4D, the valves 6 are opened at the leading end of the large diameter portion 7. After the tampon 3 is fitted in the large diameter portion 7, the valves 6 is thermally deformed into the curved face portion 7a.

The outer cylinder 1 is provided with a small diameter portion 8 on the side of the root end with respect to the center of the outer cylinder 1, and a root end 9 is diametrically enlarged to form an opening 10.

The inner cylinder 2 is formed of an extruded material by extrusion-molding a thermoplastic resin such as PE, PP or PET (i.e., polyethylene terephthalate) into a cylindrical shape (e.g., a straw shape or a pipe shape). More preferably, the extruded thermoplastic resin is oriented in the axial direction. The extruded material thus extrusion-molded and axially oriented is improved in the axial orientation so that its axial buckling strength is enhanced. Even if the thickness is made so small as 0.4 mm or less (up to about 0.1 mm) whereas the internal diameter is made so small as 7 mm or less (up to about 3 mm), the inner cylinder 2 retains a sufficient buckling strength. Accordingly, the inner cylinder 2 is hardly buckled or not folded, when the inner cylinder 2 is pushed to push out the tampon 3 from the protruding mouth 5 of the outer cylinder 1 upon use.

The inner cylinder 2 is movably inserted into the small diameter portion 8 of the outer cylinder 1 and has a push portion 11 at its front end. This push portion 11 is diverged to easily push the tampon 3 from its rear end and to prevent the inner cylinder 2 from being withdrawn from a root end 9 of the outer cylinder 1. Therefore, the external diameter D1 (see FIG. 2B) of the push portion 11 is made larger than the internal diameter d of the small diameter portion 8 of the outer cylinder 1.

On the other hand, at the rear end of the inner cylinder 2, there is formed a diverging portion 12. By forming the diverging portion 12, the inner cylinder 2 can be easily pushed, even though slender, at its rear end with a finger of the user. Furthermore, the external diameter D2 of the diverging portion 12 is made larger than the internal diameter of the root end of the outer cylinder 1 to prevent the diverging portion 12 from entering into the outer cylinder 1 from the opening 10.

The push portion 11 to be formed at the front end of the inner cylinder 2 is preferably formed into such a shape that the external diameter becomes gradually larger toward the front end, as shown in FIGS. 1 and 2B. The sectional shape of a diverging wall 11a of the push portion 11 is linearly changed so that the external diameter becomes gradually larger, as shown in FIG. 2B, whereby the push portion 11 may be counter-tapered. On the other hand, it may be formed into a bugle shape so that the external diameter of the sectional shape of the diverging wall 11a becomes gradually larger in a curved face shape toward the front end.

Furthermore, at an edge portion of the front end of the diverging wall 11a, there is formed a bent portion 11b. In the shown embodiment of FIG. 2B, the bent portion 11b is formed by outwardly rounding the edge portion of the diverging wall 11a. However, this bent portion 11b may be formed by outwardly folding the edge portion into two. On the other hand, the bent portion 11b may be rounded inwardly of the diverging wall 11a or folded into two inwardly thereof.

Since the push portion 11 is formed with the bent portion 11b, the contact with an edge is not felt by the body to give no uncomfortable feeling to the body, even if the push portion 11 comes into contact with the vaginal cavity when the tampon 3 is pushed out thereinto.

Furthermore, as shown in FIG. 3, it is preferred that the width W of the bent portion 11b is smaller than the diameter Da of the take-out cord 4. By the width W of the bent portion 11b, a clearance is established between the bent portion 11b and the inner wall of the outer cylinder 1. Accordingly, in case where the width W is excessively large, the leading end of the take-out cord 4 tends to be caught in the clearance between the bent portion 11b and the inner wall of the outer cylinder 1, when it is inserted into the inner cylinder 2. As a result, it becomes difficult to put the take-out cord 4 through the inner cylinder 2.

The push portion 11 can be easily formed by pushing a heated press die 15 as shown in FIG. 2B, onto the front portion of the inner cylinder 2. With the press die 15, there are formed a tapered portion 15a which is located at the central portion, and a groove 15b which is extended circumferentially in the bottom portion of the tapered portion 15a. By heating the press die 15 and applying it to the front end of the inner cylinder 2, the diverging wall 11a can be formed by the tapered portion 15a, and the edge portion of the diverging wall 11a can be bent by the groove 15b.

As shown in FIG. 2A, the diverging portion 12 at the rear end of the inner cylinder 2 is also preferably formed into the counter-tapered shape or the bugle shape. Furthermore, an edge portion of the rear end of the diverging portion 12 is rounded or folded into two outwardly or inwardly of a diverging portion 12a to form a bent portion 12b. By forming this bent portion 12b, the finger of the user is to contact the bent portion 12b, when the diverging portion 12 is pushed by the finger, so that the resistance to the finger can be reduced.

This diverging portion 12 can also be easily formed by pushing a press die, which has the same shape as but a slightly smaller size than the press die 15 shown in FIG. 2B, onto the rear end of the inner cylinder 2.

It should be noted that the push portion 11 and the diverging portion 12 should not necessarily be limited in the counter-tapered shape or the bugle shape. For example, the push portion 11 and the diverging portion 12 may be formed by expanding the body portion of the inner cylinder 2, while keeping their external shapes, generally into the cylindrical shape.

FIGS. 4A to 4D show respectively a step of one example of the method for manufacturing the tampon applicator.

Figure 4A:
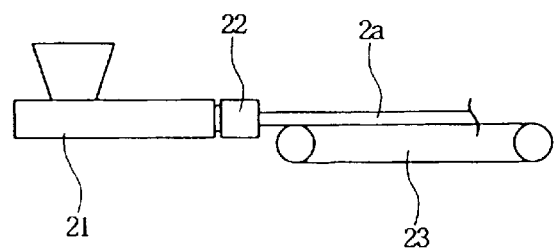
FIGS. 4A, 4B, 4C and 4D are explanatory diagrams showing one embodiment of a method for manufacturing the applicator.

As shown in FIG. 4A, a thermoplastic resin is melted and extruded by a melt extruder 21, shaped by a die 22 into a cylindrical (e.g., straw or pipe) shape, axially oriented by an orienting delivery unit 23, and cooled to form an extruded material 2a.

Figure 4B:
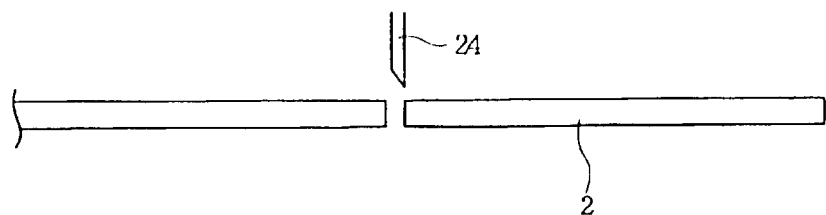
Figure 4C:
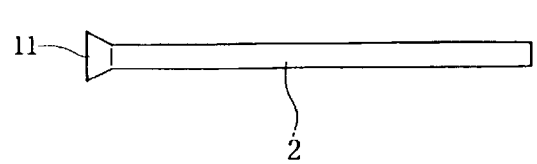
Figure 4D:
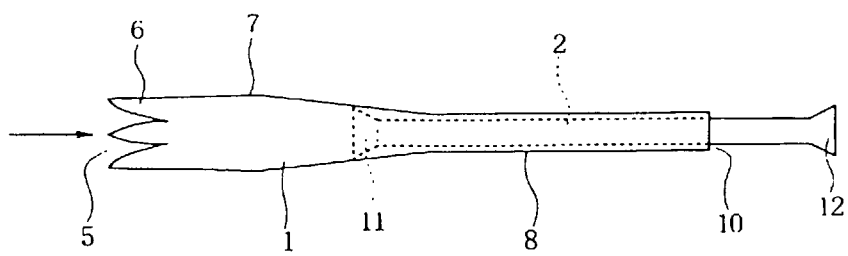

In FIG. 4B, the extruded material 2a is cut by a cutter 24 to obtain a predetermined length of the inner cylinder 2. After this, as shown in FIG. 4C, the press die 15 is heated and pushed onto the front end of the inner cylinder 2 to form the counter-tapered (or bugle shaped) push portion 11.

On the other hand, the outer cylinder 1 is injection-molded into the shape shown in FIG. 4D. The rear end of the inner cylinder 2 before being formed with the push portion 11, is inserted from the protruding mouth 5 at the leading end of the outer cylinder 1, and is put through the small diameter portion 8 so that it is projected rearwardly from the opening 10 at the root end 9. After that, the press die is heated and pushed onto the rear end of the inner cylinder 2 to form the diverging portion 12.

The tampon 3 is inserted from the protruding mouth 5 into the large diameter portion 7 of the outer cylinder 1. At this time, the take-out cord 4 is pulled out rearwardly through the inner cylinder 2. After that, the valves 6 around the protruding mouth 5 of the outer cylinder 1 are thermally deformed so that the protruding mouth 5 is plugged with the curvedly deformed valves 6, as shown in FIG. 1.

According to the invention set forth above, the inner cylinder of the applicator is formed of the extruded material so that it can be manufactured at a lower cost than that of the injection-molded one. It is also possible to lower the cost for changing the diameter or shape of the inner cylinder. Furthermore, the inner cylinder thus formed of the extruded material can freely select its thickness or diameter so that it can be made thin or diametrically small to reduce the amount of resin to be employed. In this case, the buckling strength in the axial direction thereof can be enhanced if the extruded material to be employed is axially oriented. Furthermore, the push portion at the front end and the diverging portion at the rear end of the inner cylinder can be easily shaped.

While the invention has been described in detail and with reference to specific embodiments thereof, it will be apparent to one skilled in the art that various changes and modifications can be made therein without departing from the spirit and scope thereof.

Here, 'comprises/comprising' when used in this specification is taken to specify the presence of stated features, integers, steps or components but does not preclude the presence or addition of one or more other features, integers, steps, components or groups thereof.

What is claimed is:

1. An applicator with a tampon comprising:
    an outer cylinder including leading and root ends, a protruding mouth for ejecting the tampon formed at the leading end, and an opening formed at the root end;
    an inner cylinder for pushing out the tampon, and said inner cylinder having a front end located in said outer cylinder and a rear end protruding rearwardly from said outer cylinder through said opening; and
    said inner cylinder being made of an extruded thermoplastic resin composition tubing, one end of said tubing being deformed to define a push portion of said inner cylinder, said push portion having a larger diameter and an outwardly or inwardly bent portion about the periphery thereof.

2. An applicator with a tampon as set forth in claim 1, wherein said outer cylinder includes a large diameter portion for fitting said tampon therein, and a small diameter portion extending from said large diameter portion toward the root end, and wherein said push portion of said inner cylinder is positioned in said large diameter portion and has a larger external diameter than an internal diameter of said small diameter portion.

3. An applicator with a tampon as set forth in claim 1, wherein said extruded material is extrusion-molded and then axially oriented.

4. An applicator with a tampon as set forth in claim 1, wherein said push portion has an external diameter which is gradually diverged toward the front end thereof.

5. An applicator with a tampon as set forth in claim 1, wherein said inner cylinder is provided at the rear end thereof with a diverging portion which is deformed to have a diameter gradually enlarged toward the rear end.

6. An applicator with a tampon as set forth in claim 5, wherein said diverging portion formed at the rear end of said inner cylinder has an outwardly or inwardly bent portion about a periphery of said diverging portion.

7. An applicator with a tampon as set forth in claim 1, wherein each of said outwardly or inwardly bent portion has a dimension smaller than a thickness of a take-out cord extending from said tampon.

8. An applicator with a tampon comprising:

an outer cylinder including leading and root ends, a large diameter portion for fitting said tampon therein, a protruding mouth formed at the leading end for ejecting the tampon, an opening formed at the root end, and a small diameter portion extending from said large diameter portion toward the root end;

an inner cylinder for pushing out the tampon, said inner cylinder having a front end located in said outer cylinder, a rear end protruding rearwardly from said outer cylinder through said opening, and said inner cylinder being made of an extruded axially oriented thermoplastic resin cylindrical material, one end of said cylindrical material being deformed to define a push portion at a front end of said inner cylinder, said push portion having a larger diameter at a front end thereof and an outwardly or inwardly bent portion about the periphery of said push portion;

wherein said push portion of said inner cylinder is positioned in said large diameter portion and has a larger external diameter than an internal diameter of said small diameter portion.

9. An applicator with a tampon comprising:

an outer cylinder including leading and root ends, a protruding mouth for ejecting the tampon formed at the leading end, and an opening formed at the root end;

an inner cylinder for pushing out the tampon, and having a front end located in said outer cylinder and a rear end protruding rearwardly from said outer cylinder through said opening; and said inner cylinder being made of an extruded thermoplastic resin composition tubing, another end of said tubing being deformed to define a diverging portion of said inner cylinder, said diverging portion having a larger diameter and an outwardly or inwardly bent portion at the periphery thereof.

* * * * *